US011952570B2

(12) United States Patent
Shoura et al.

(10) Patent No.: US 11,952,570 B2
(45) Date of Patent: Apr. 9, 2024

(54) METHODS FOR RAPID SEPARATION AND PURIFICATION OF DNA TOPOLOGICAL FORMS

(71) Applicants: The Board of Trustees of the Leland Stanford Junior University, Stanford, CA (US); BOARD OF REGENTS, THE UNIVERSITY OF TEXAS SYSTEM, Austin, TX (US)

(72) Inventors: Massa Shoura, Stanford, CA (US); Stephen Levene, Redwood City, CA (US); David Girata, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/098,615

(22) Filed: Jan. 18, 2023

(65) Prior Publication Data
US 2023/0151349 A1     May 18, 2023

Related U.S. Application Data

(63) Continuation of application No. PCT/US2021/042594, filed on Jul. 21, 2021.

(60) Provisional application No. 63/064,261, filed on Aug. 11, 2020, provisional application No. 63/055,029, filed on Jul. 22, 2020.

(51) Int. Cl.
*C12N 15/10* (2006.01)
(52) U.S. Cl.
CPC ..... *C12N 15/1006* (2013.01); *C12N 15/1003* (2013.01)
(58) Field of Classification Search
CPC .............. C12N 15/1006; C12N 15/1003
See application file for complete search history.

(56) References Cited

U.S. PATENT DOCUMENTS

2003/0032147 A1     2/2003 Sauer et al.

OTHER PUBLICATIONS

Phillips WH et al. High resolution KSCN/CsSCN Equilibrium Gradients Effectively Separate a Population of Density Labeled Proteins from Unlabeled Proteins. 1989. Analytical Biochemistry. 177, 333-340. (Year: 1989).*
Zilberman D et al. Genome-wide analysis of DNA methylation patterns. 2007. Development. 134, 3959-3964. (Year: 2007).*
Koob M et al. Preparing and Using Agarose Microbeads. 1992. Methods in Enzymology. vol. 216. p. 13-20. (Year: 1992).*
Posfai G et al. In vivo excision and amplification of large segments of the *Escherichia coli* genome. 1994. Nucleic Acids Research. vol. 22, No. 12. 2392-2398. (Year: 1994).*
Shoura et al. (2017) "Intricate and Cell Type-Specific Populations of Endogenous Circular DNA (eccDNA) in Caenorhabditis elegans and *Homo sapiens*. G3 (Bethesda)", vol. 7, No. 10, p. 3295-3303.
Marziali et al. (1999) "An arrayable flow-through microcentrifuge for high-throughput instrumentation." Proc. Natl. Acad. Sci. USA, vol. 96, No. 1, pp. 61-66.

* cited by examiner

*Primary Examiner* — Paul J Holland
(74) *Attorney, Agent, or Firm* — Pamela J. Sherwood; Bozicevic, Field and Francis LLP

(57) ABSTRACT

Methods are provided for the isolation and analysis of circular DNA from complex samples, based on the topology of the DNA molecule. A sample comprising DNA species is combined with a chaotropic dense salt solution. A fraction containing the circular DNA of interest is isolated and dialyzed to remove excess salt. In some embodiments salt gradients are generated by ultracentrifugation in the absence of intercalating dyes, e.g. ethidium bromide; and in the absence of protease digestion. The circular DNA thus isolated is substantially pure, e.g. greater than about 75%, greater than about 80%, greater than about 90%, greater than about 95% of DNA in the isolated fraction is comprised of circular DNA.

21 Claims, 3 Drawing Sheets

Fraction 1 Additional Regions

METHODS FOR RAPID SEPARATION AND PURIFICATION OF DNA TOPOLOGICAL FORMS

CROSS REFERENCE TO RELATED APPLICATION

The present application is a Continuation and claims the benefit of PCT Application No. PCT/US2021/042594, filed Jul. 21, 2021, which claims priority to U.S. Provisional Patent Application No. 63/055,029 filed Jul. 22, 2020, and U.S. Provisional Patent Application No. 63/064,261 filed Aug. 11, 2020, which applications are incorporated herein by reference in their entirety.

GOVERNMENT SUPPORT RESEARCH

This invention was made with government support under Grant no. 70NANB18H026 awarded by the National Institute of Standards and Technology, and Grant no. R01 GM117595 awarded by the National Institutes of Health. The government has certain rights in the invention.

BACKGROUND

Circular DNA formation is widespread in nature, with many examples of eukaryotes and prokaryotes utilizing this phenomenon to rapidly generate genetic variation and amplify copy number.

Extrachromosomal-circular DNA (eccDNA, microDNA, double minutes, or ecDNA), a distinct topological form of DNA, is emerging as a potential biomarker for genomic variation, cancer, and other diseases. For example, it has been shown that 40% of cancers contain these extrachromosomal elements and their presence can negatively affect the outcome of the disease. Because this form constitutes a tiny mass fraction of an organism's DNA, techniques for isolation or enrichment within genomic-DNA samples are needed to advance basic research in circular-DNA biology and applications such as molecular diagnostics. However, purification of large circular DNAs has been extremely technically challenging due to a high probability of DNA breakage and degradation.

The present disclosure provides methods for the efficient isolation of DNA circles based on their topology.

SUMMARY

Methods are provided for the isolation and analysis of circular DNA from complex samples, based on the topology of the DNA molecule. A sample comprising DNA species is combined with a chaotropic dense salt solution, and ultracentrifuged to generate a gradient in which different DNA topologies are stratified. The fraction containing the circular DNA of interest is then isolated and dialyzed to remove excess salt. In some embodiments, the salt gradients are generated in the absence of intercalating dyes, e.g. ethidium bromide; and in the absence of deproteinization using proteolytic enzymes or by other means. In some embodiments, the circular DNA is isolated from a chaotropic salt suspension in the absence of ultracentrifugation, e.g. by utilizing reannealing properties to distinguish circular DNA. The topology of the circular DNA thus isolated is substantially pure, e.g. greater than about 90%, greater than about 95%, greater than about 98% of DNA in the isolated fraction is comprised of circular DNA.

In some embodiments a cell sample for analysis, comprising a whole organism, tissue, cells in suspension, or cells/tissue embedded in a polymer matrix is resuspended in the chaotropic dense salt solution. Polymer matrixes of the present disclosure include without limitation, agarose, hydrogel, alginate, or Pluronic polymers at concentrations sufficient to inhibit degradation of DNA by mechanical shearing. Matrices optionally comprise an antibody, aptamer, fluorophore, or another tag to improve specificity. The embedded cells may be lysed in situ, and the matrix dissolved in the chaotropic dense salt solution. The matrix is dissolved by the chaotropic salt at ambient temperature, e.g. from about 10° C. to about 40° C. Purification can then proceed as described above.

In some embodiments the circular DNA is eccDNA, double minutes (ecDNA), or microDNA present in eukaryotic cells. eccDNA comprises all circular DNAs. microDNAs are small eccDNA. Larger circles that are present in cancer cells, or in cells that harbor a resistance gene, are historically referred to as double minutes. In some embodiments the ecDNA is present in a bodily fluid, e.g. plasma, synovial fluid, CSF, and the like.

The circular DNA may be isolated by the methods described herein from a complex sample comprising the nuclear DNA present in a eukaryotic cell; and may also be isolated from a complex sample comprising the total DNA present in a eukaryotic cell, e.g. including mitochondrial DNA, etc., and/or the complex DNA present in circulating samples. The ecDNA may be present as a small fraction of the total nuclear DNA in a cell, e.g. having a copy number of less than about 500, less than about 250, less than about 100, less than about 50, less than about 10, or less than about 5 copies per cell, on average over the sample. The ecDNA may share sequences with chromosomal DNA in the cell, e.g. as amplified or mutated copies of endogenous oncogenes, and the like.

In some embodiments the circular DNA is present in a supercoiled, dsDNA configuration. The circular DNA may be up to about 100 bp in length, up to about 500 bp in length, up to about 1 kbp, up to about 5 kbp, up to about 10 kbp, up to about 25 kbp, up to about 35 kbp, up to 50 kbp or more. In some embodiments the circular DNA is greater than 50 kbp.

In some embodiments the circular DNA is present in a chromatin configuration in the sample from which it is isolated. In some embodiments the chromatin configuration is maintained during the isolation process. In other embodiments the circular DNA is present as naked DNA in the same form in which it is isolated, i.e. not complexed with histones or other proteins. Samples, including DNA in a chromatin configuration, may comprise DNA with covalent modifications or histone modifications, or both.

Samples for circular DNA isolation comprise various tissues, bodily fluids, etc. In some embodiments the sample comprises less than about $10^3$ cells, e.g. less than about 6-10 ng of genomic DNA. Samples may comprise less than about $10^4$ cells, less than about $10^5$ cells, less than about $10^6$ cells, less than about $10^7$ cells. In some embodiments a cell sample comprises suspected tumor cells, e.g. blood samples, biopsy samples, and the like. Samples may comprise DNA bearing covalent modifications, e.g. methylated cytosine, etc. Samples may be immunoprecipitated or affinity-isolated and selected for marks and modification prior to purification. The scale of the assay can be further optimized for small cell samples, e.g. up to about 10 cell, up to about $10^2$ cells, up to about $10^3$ cells, single cells, etc. A small number of reads, e.g. from about $1$-$10^3$, from about $1$-$10^2$, from about 1-10, etc. reads provides sufficient information to identify the circular DNA present in the sample.

The isolated fraction of circular DNA can be analyzed by any convenient method for physical or sequence parameters, including without limitation sequencing, imaging, epigenetic analysis, copy-number quantification, and topological characterization. For example, any NGS pipeline may be used, including NGS workflows that can be coupled to probing DNA and nucleosome epigenetic modifications.

DETAILED DESCRIPTION

Figure 1:
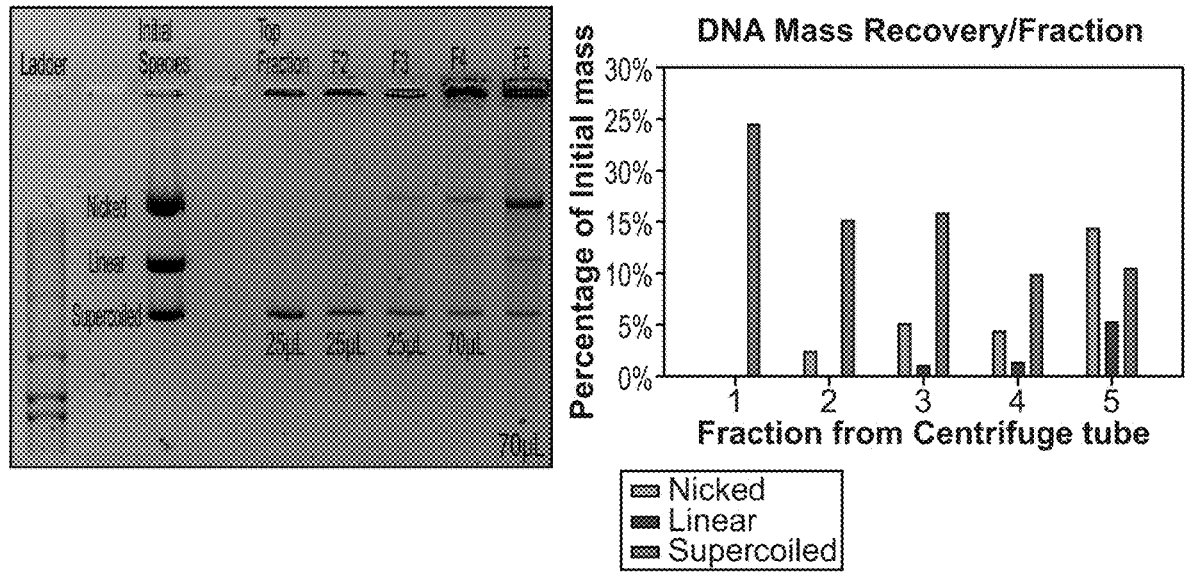
FIG. 1. Fractionation of different circular-DNA topological forms for a 4.0-kbp plasmid DNA. Fractions of an equimolar mixture consisting of nicked (N), linear (L), and supercoiled (S) forms of a 4.0-kbp plasmid subjected to density-gradient centrifugation according to the method described herein. The agarose gel shows the composition of fractions 1-5 (top to bottom of the gradient). The gel bands in the far-left lane are (top to bottom) N, L, S. The graph shows the relative abundance (mass fraction relative to DNA input of the given species) as a function of fraction number. Overall yield of each species is given in the bottom table.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure and are not meant to be limiting in any fashion.

The terms "individual," "host," "subject," and "patient" are used interchangeably herein, and refer to an animal, including, but not limited to, any eukaryotic species, e.g. plants, animals, fungus, etc.; which may include mammals. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations. Of interest are human and non-human primates, including simians and humans; rodents, including rats and mice; bovines; equines; ovines; felines; canines; avians, and the like.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "determining," "measuring," "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular, e.g. closed circles which may be supercoiled.

ecDNAs are a class of circular DNA structures found in eukaryotic cells that are other than a conventional chromosome. The sequence of an ecDNA may be similar or identical to sequences present in conventional chromosomes, but the ecDNA is topologically distinct. They may be referred to as extrachromosomal circular DNA, or eccDNA. They are distinguished from other DNA structures by their size and constituents; usually ranging between 0.2-5 Mbp in length and frequently contain one or more oncogenes and regulatory elements.

Circular structures as large as ecDNA are rarely detected in healthy human cells; however, smaller eccDNAs, structures that range from 100 bp to 100 kbp, can be detected in both healthy and cancer cells. The repertoire of these eccDNAs is determined by cell type, developmental stage, and pathology. Oncogenes expressed on ecDNA significantly amplify copy number through random segregation of amplicons during mitosis. EGFR, MYC, CCND1, CDK4 and MDM2 are commonly amplified oncogenes.

ecDNA have been shown to dynamically re-integrate onto aberrant genomic locations known as homogenous staining regions (HSRs). These are highly duplicated intrachromosomal regions that stain uniformly on cytogenetic Giemsa-banding. Consequently, gene amplification has been classically divided by these cytogenetic techniques; intrachromosomal HSRs and extrachromosomal DMs. HSRs also form as consequence of complex genomic rearrangements such tandem duplications and chromosome breakage-fusion cycles.

Chromatin modifying enzymes and epigenetic states are involved in ecDNA oncogene copy-number amplification. For example, histone lysine methyltransferases (KMT) and demethylases (KDM) modulate histone methylation balance and subsequent transient site-specific copy gains. The chromatin topology of ecDNA can contribute towards positive selection and cell fitness through proximity to regulatory elements and accessibility to transcription machinery. The nucleosomal organization of ecDNA is less compacted compared with linear DNA, allowing for highly accessible chromatin that remains organized. ecDNA enables ultra-long-range chromatin contacts, permitting distant interactions with regulatory elements.

Double minutes are small fragments of extrachromosomal DNA, which have been observed in a large number of human tumors including breast, lung, ovary, colon, and most notably, neuroblastoma. They are a manifestation of gene amplification as a result of chromothripsis, during the development of tumors, which give the cells selective advantages for growth and survival. This selective advantage is as a result of double minutes frequently harboring amplified oncogenes and genes involved in drug resistance. Double minutes, like actual chromosomes, are composed of chromatin and replicate in the nucleus of the cell during cell division. Unlike typical chromosomes, they are composed of circular fragments of DNA, up to only a few million base pairs in size and contain no centromere or telomere. Further to this, they often lack key regulatory elements, allowing genes to be constitutively expressed.

MicroDNAs are <400-base extrachromosomal circles found in mammalian cells. Tens of thousands of microDNAs have been found in all tissue types, including sperm. MicroDNAs arise preferentially from areas with high gene density, GC content, and exon density from promoters with activating chromatin modifications and in sperm from the 5'-UTR of full-length LINE-1 elements, but are depleted from lamin-associated heterochromatin. Analysis of microDNAs from a set of human cancer cell lines revealed lineage-specific patterns of microDNA origins. Evidence suggests that microDNAs arise as part of normal cellular physiology—either from DNA breaks associated with RNA metabolism or from replication slippage followed by mismatch repair.

Chromatin structure, as used herein, refers to the configuration of DNA and histone proteins. The structure may be a typical "beads on a string" nucleosome structure of histones. With addition of H1, the beads-on-a-string structure may be organized into a prototypical 30-nm diameter helical structure known as the 30-nm fiber or filament (heterochromatin). The histone proteins may be modified by various post-translational modifications to alter packing, for example lysine methylation, etc.

DNA structures may be naturally present in a sample in a chromatin structure. DNA structures may also be induced, synthetically or in a cell, to assume a chromatin structure, which may be referred to as chromatinization.

Chaotropic salt. A chaotropic agent disrupts the structure of, and denatures, macromolecules such as proteins and nucleic acids. Chaotropic salts that dissociate in solution exert chaotropic effects by shielding charges and preventing the stabilization of salt bridges. Hydrogen bonding is stronger in non-polar media, so salts, which increase the chemical polarity of the solvent, can also destabilize hydrogen bonding.

Empirical tables such as the Hofmeister series are available that delineate these ions and rank order them with respect to their effects on nucleic-acid and protein structures, providing guidance for selection of an agent. For example, see Hyde et al. (2017). "General Principles and Strategies for Salting-Out Informed by the Hofmeister Series". Organic Process Research & Development. 21 (9): 1355-1370, herein specifically incorporated by reference. Salts of interest for use in the methods disclosed herein include, without limitation, Rb trichloroacetic acid (TCA), CsTCA, BaTCA, Rb thiocynanate (SCN), CsSCN, etc. and combinations thereof.

Dense chaotropic-salt solution. The range of working molarities for a chaotropic salt solution for the methods disclosed herein are narrow. In the case of RbTCA, the working stock concentration of the solution is from about 5.1+/−0.1M. The final molarity of the DNA-RbTCA solution is between about 4M to 4.3M before centrifugation and gradient formation. The specific molarity for other chaotropic salts or mixtures of chaotropic salts can be empirically determined, e.g. relative to the exemplified RbTCA solution.

Matrix and polymers. In some embodiments a suspension of cells is embedded in a matrix, including without limitation a natural or synthetic hydrogel. Various polymers find use for this purpose, with the general requirement that the polymer matrix structure can be formed around cells under physiologically acceptable conditions and will be dissolved in the chaotropic salt solution at ambient temperatures. Polymers may be used as a matrix at a concentration sufficient to inhibit degradation of DNA by mechanical shearing, which varies by the specific polymer but is generally from 0.1 to about 10%. Preferred polymers are free of nucleases.

Some examples of biodegradable polymers useful in the present invention include: hydroxyaliphatic carboxylic acids, either homo- or copolymers, such as polylactic acid, polyglycolic acid, polylactic glycolic acid; polysaccharides such as cellulose or cellulose derivatives such as ethyl or methyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthalate and calcium alginate, polypropylene, polybutyrates, polycarbonate, acrylate polymers such as polymethacrylates, polyanhydrides, polyvalerates, polycaprolactones such as poly-epsilon-caprolactone, polydimethylsiloxane, polyamides, polyvinylpyrollidone, polyvinylalcohol phthalate, gelatin, agarose, starch, alginate, reversibly cross-linked hydrogels, elastin polypeptides, hyaluronan, PEG, HEMA, PHEMA, EGDMA, TEGDMA-cross linked polymers, Acrylamide/acrylic polymers, Chitosan, Heprin, etc.

Of interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof.

Polysaccharides useful as a matrix include calcium alginate, and functionalized celluloses, particularly carboxymethylcellulose esters characterized by being water insoluble, molecular weight of about 5 kD to 500 kD, etc. Other polymers of interest include polyvinyl alcohol, esters and ethers, which are biocompatible and may be biodegradable or soluble.

Biocompatible, non-biodegradable polymeric compositions are also used as a matrix. Various non-biodegradable polymers which may be employed are described in U.S. Pat. Nos. 4,303,637; 4,304,765; 4,190,642; 4,186,184; 4,057,619; 4,052,505; 4,281,654; 4,959,217; 4,014,335; 4,668,506; 4,144,317. The non-biodegradable polymers may be homopolymers, copolymers, straight, branched-chain, or cross-linked derivatives.

Biocompatible, non-biodegradable polymers of particular interest include polycarbamates or polyureas, particularly polyurethanes, polymers which may be cross-linked to produce non-biodegradable polymers such as cross-linked poly (vinyl acetate) and the like. Also of particular interest are ethylene-vinyl ester copolymers having ail ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentantoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer.

Additional naturally occurring or synthetic non-biodegradable polymeric materials include poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), poly(trifluorochloroethylene), chlorinated poly(ethylene), poly(4,4'-isopropylidene diphenylene carbonate), vinylidene chloride-acrylonitrile copolymer, vinyl chloride-diethyl fumarate copolymer, silicone, silicone rubbers (especially the medical grade), poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls), poly(acrylate), poly(methacrylate), poly(oxides), poly(esters), poly(amides), and poly(carbonates).

Matrices may comprise an antibody, aptamer, fluorophore, or another tag to improve specificity.

Cells. Cells for use in the assays of the invention can be an organism, a tissue sample, including a biopsy sample, etc. The invention is suitable for use with any cell type, including primary cells, biopsy tissue, etc.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. Tumors of interest for analysis include carcinomas, e.g. colon, prostate, breast, melanoma, ductal, endometrial, stomach, dysplastic oral mucosa, invasive oral cancer, non-small cell lung carcinoma, transitional and squamous cell urinary carcinoma, etc.; neurological malignancies, e.g. neuroblastoma, gliomas, etc.; hematological malignancies, e.g. childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Cells for use in the assays of the invention may be cancer cells. The types of cancer cells that may be used in the present disclosure, include without limitation, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia cells.

Cells are optionally sorted, e.g. by flow cytometry, prior to the analysis. For example, FACS sorting or size-differential sorting, can be used to increase the initial concentration of the cells of interest by at least 1,000, 10,000, 100,000, or more fold, according to one or more markers present on the cell surface, e.g. B220, CD3, CD4, CD8, CD25, CD16, CD19, etc. Such cells are optionally sorted according to the presence and/or absence of cell surface markers particularly markers of a population or subpopulation of interest. Analysis of cell staining can be performed using conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide, ethidium monoazaide (EMA), etc.).

One approach is the use of antibodies as affinity reagents. Conveniently, these antibodies can be conjugated with a label for use in separation. Labels include any labels known in the art including, but not limited to, magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

Antibodies can be added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated is any medium that maintains the viability of the cells. One medium which can be utilized is phosphate buffered saline containing from 0.1 to 0.5% BSA. Various media are commercially available and may be used according to the nature of the cells, including Dulbecco's Modified Eagle Medium (dMEM), Hank's Basic Salt Solution (HESS), Dulbecco's phosphate buffered saline (dPBS), RPMI, Iscove's medium, PBS with 5 mM EDTA, etc., frequently supplemented with fetal calf serum, BSA, HSA, etc. The labeled cells can then be quantitated as to the expression of cell surface markers as previously described.

For isolation of cells from tissue, an appropriate solution can be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The separated cells can be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Lysates. Cells may be lysed prior to purification. Methods of lysis are known in the art, including sonication, ionic or non-ionic surfactants, etc. Ionic surfactants may be of anionic type such as sodium dodecyl sulfate, sodium lauryl ether sulfate, and sodium myreth sulfate, or cationic type such as octenidine dihydrochloride, cetrimonium bromide, cetylpyridinium chloride, benzalkonium chloride, benzethonium chloride, dimethyl dioctadecyl ammonium chloride, and dioctadecyl dimethyl ammonium bromide Non-ionic surfactants include the Triton™ family of detergents, e.g. Triton™ X-15; Triton™ X-35; Triton™ X-45; Triton™ X-100; Triton™ X-102; Triton™ X-114; Triton™ X-165, etc. Brij™ detergents are also similar in structure to Triton™ X detergents in that they have varying lengths of polyoxyethylene chains attached to a hydrophobic chain. The Tween™ detergents are nondenaturing, nonionic detergents, which are polyoxyethylene sorbitan esters of fatty acids. Tween™ 80 is derived from oleic acid with a $C_{18}$ chain while Tween™ 20 is derived from lauric acid with a $C_{12}$ chain. The zwitterionic detergent, CHAPS, is a sulfobetaine derivative of cholic acid. This zwitterionic detergent is useful for membrane protein solubilization when protein activity is important. The surfactant is contacted with the cells for a period of time sufficient to lyse the cells.

Methods of cellular fractionation are also known in the art. Subcellular fractionation consists of two major steps, disruption of the cellular organization (lysis) and fractionation of the homogenate to separate the different populations of organelles. Such a homogenate can then be resolved by differential centrifugation into several fractions containing mainly (1) nuclei, heavy mitochondria, cytoskeletal networks, and plasma membrane; (2) light mitochondria, lysosomes, and peroxisomes; (3) Golgi apparatus, endosomes and microsomes, and endoplasmic reticulum (ER); and (4) cytosol.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

As used herein, the terms "treatment," "treating," and the like, refer to obtaining a desired pharmacologic and/or physiologic effect, such as reduction of viral titer. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease (e.g., reduction in viral titers).

Amplification refers to the process by which DNA templates are increased in number through multiple rounds of replication. Isolated circular DNA can be amplified in vitro, for example. Conveniently, polymerase chain reaction (PCR) is the method of in vitro amplification, but such is not required, and other methods, such as loop-mediated isothermal amplification (LIA); ligation detection reaction (LDR); ligase chain reaction (LCR); nucleic acid sequence based amplification (NASBA); multiple displacement amplification (MDA); C-probes in combination with rolling circle amplification; and the like may find use. See, for example, Kozlowski et al. (2008) Electrophoresis. 29(23):4627-36; Monis et al. (2006) Infect Genet Evol. 6(1):2-12; Zhang et al. (2006) Clin Chim Acta. 363(1-2):61-70; Cao (2004) Trends Biotechnol. 22(1):38-44; Schweitzer and Kingsmore (2001) Curr Opin Biotechnol. 12(1):21-7; Lisby (1999) Mol Biotechnol. 12(1):75-99. As known in the art, amplification reactions can be performed in a number of configurations, e.g. liquid phase, solid phase, emulsion, gel format, etc.

It is preferable to utilize a high-fidelity polymerase in the amplification reaction to preserve sequence integrity, typically a polymerase having an intact proof-reading function, e.g. Pfx50™ DNA Polymerase; Pfu polymerase, Vent polymerase, Phusion High-Fidelity DNA Polymerase; and the like.

Primers may comprise nucleotides useful in subsequent sequencing. Such sequences are readily designed by commercially available software programs or companies (e.g. see Biotage). Amplification primers may optionally include a barcode sequence, to aid in the identification of clones (see Parameswaran et al. (2007) Nucleic Acids Research 35(19): e30, herein specifically incorporated by reference).

Samples may be sequenced by any convenient method, e.g. by Next Generation Sequencing (NGS), which is a powerful platform that has enabled the sequencing of thousands to millions of DNA molecules simultaneously. A variety of technologies are known and used in the art. In pyrosequencing, the sequencing reaction is monitored through the release of the pyrophosphate during nucleotide incorporation. Sequencing by synthesis utilizes the step-by-step incorporation of reversibly fluorescent and terminated nucleotides for DNA sequencing and is used by the Illumina NGS platforms. Sequencing by ligation relies on short oligonucleotide probes that are ligated to one another. The sequencing reaction commences by binding of the primer to the adapter sequence and then hybridization of the appropriate probe. Ion semiconductor sequencing utilizes the release of hydrogen ions during the sequencing reaction to detect the sequence of a cluster. Each cluster is located directly above a semiconductor transistor which is capable of detecting changes in the pH of the solution. During nucleotide incorporation, a single H+ is released into the solution and it is detected by the semiconductor.

Sequencing platforms include, but are not limited to those commercialized by: Oxford Nanopore, Illumina, 454/Roche Lifesciences including but not limited to the methods and apparatus described in Margulies et al., Nature (2005) 437: 376-380 (2005); and U.S. Pat. Nos. 7,244,559; 7,335,762; 7,211,390; 7,244,567; 7,264,929; 7,323,305; Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; Applied Biosystems (e.g. SOLiD sequencing); Dover Systems (e.g., Polonator G.007 sequencing); Illumina as described U.S. Pat. Nos. 5,750,341; 6,306,597; and 5,969,119; and Pacific Biosciences as described in U.S. Pat. Nos. 7,462,452; 7,476, 504; 7,405,281; 7,170,050; 7,462,468; 7,476,503; 7,315, 019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated (e.g. host cell proteins).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.).

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

METHODS

A biological sample comprising DNA species in multiple topological states, including circular DNA, is prepared. In some embodiments the sample is fixed, e.g. with addition of formaldehyde or the equivalent to a concentration of around about 0.75%. Alternatively the sample can be embedded in a matrix as described herein, at a concentration that prevents DNA damage (typically matrix-dependent and in a range between 0.1 and 10%). In some embodiments, the concentration of matrix is from 0.5% to 10%, 1-10%, 1.5%-10%, 2-10%, 2.5-10%, 3-10%, 3.5%-10%, 4-10%, 4.5%-10%, 5-10%, 5.5%-10%, 6%-10%, 6.5%-10%, 7%-10%, 7.5%-10%, 8%-10%, 8.5%-10%, 9%-10%, or from 9.5-10%. In some embodiments, the matrix is does not contain nucleases or is devoid of any nuclease activity. In some embodiments a matrix comprises one or more of an antibody, aptamer, fluorophore, or another tag to improve specificity.

The sample is then combined in a dense chaotropic salt solution in the absence of intercalating dyes and in the absence of deproteinization using proteolytic enzymes or by other means. In embodiments where the sample is embedded in a matrix, the chaotropic salt dissolves the matrix.

The chaotropic salt and DNA mixture can then be ultracentrifuged to generate a gradient in which different DNA topologies are stratified. The fraction containing the circular DNA of interest is then isolated and dialyzed to remove excess salt.

In some embodiments, the circular DNA of interest is isolated in the absence of centrifugation, or in the absence of ultracentrifugation. In these embodiments, the cells can be lysed directly in the chaotropic salt solution in the absence of a chaotropic salt gradient leading to release of the DNA contents, including without limitation, circular DNA, linear DNA, nicked DNA, etc. In these embodiments, the DNA of interest is double-stranded DNA. In these embodiments, only covalently closed-circular DNA is able to efficiently reanneal to from duplex DNA upon removal of the salt, but the linear and nicked-circular forms do not. In some embodiments, a single strand specific nuclease may be used to degrade all non-double stranded DNA. Single strand specific nucleases that find use in the present disclosure include without limitation, Micrococcal nuclease, S1 nuclease, Mung Bean nuclease, etc.

In some embodiments, the circular DNA of interest may be further isolated using chromatin-immunoprecipitation as described in Gilfillan et al. (2012) BMC Genomics 13:645, Adli et al. (2010) Nat. Methods 8:615-618, Shankaranarayanan et al. (2011) Nat. Methods 7:565-567, Schmidl et al. (2015) Nat. Methods 10:963-965, Zheng et al. (2015) Cell Rep 7:1505-1518, Lara-Astiaso et al. (2014) Immunogenetics Science 345:943-949, Brind'Amour et al. (2015) Nat. Commun. 6:6033, van Galen et al. (2016) Mol. Cell 1:170-80, and Cao et al. (2015) Nat. Methods 10:959-962 herein specifically incorporated by reference. Other methods may utilize, for example, any of an antibody, aptamer, fluorophore, or another tag to improve specificity.

In embodiments that either use centrifugation or that don't use centrifugation, or that don't use ultracentrifugation, the circular DNA thus isolated is substantially pure, e.g. greater than about 90%, greater than about 95%, greater than about 98% of DNA in the isolated fraction is comprised of circular DNA.

In embodiments that use either use centrifugation or embodiments that don't use centrifugation, or that don't use ultracentrifugation, the isolated fraction of circular DNA can be analyzed by any convenient method for physical or sequence parameters, including without limitation sequencing, imaging, epigenetic analysis, copy-number quantification, and topological characterization. For example, any NGS pipeline may be used, including NGS workflows that can be coupled to probing DNA and nucleosome epigenetic modifications. In some embodiments, it may be necessary to perform the methods of the present disclosure at a specified pH range. Specified pH ranges that find use in the present disclosure, may be from a pH of about 6-12, from a pH of about 6.5-12, from a pH of about 7-12, from a pH of about 7.5-12, from a pH of about 8-12, from a pH of about 8.5-12, from a pH of about 9-12, from a pH of about 9.5-12, from a pH of about 10-12, from a pH of about 10.5-12, from a pH of about 11-12, from a pH of about 6-11.5, from a pH of about 6-11, from a pH of about 6-10.5, from a pH of about 6-10, from a pH of about 6-9.5, from a pH of about 6-9, from a pH of about 6-8.5, from a pH of about 6-8, from a pH of about 6-7.5, or from a pH of about 6-7.

Also provided are reagents and kits thereof for practicing one or more of the above-described methods. The subject reagents and kits thereof may vary greatly. Reagents of interest include reagents specifically designed for use in production of the above described analysis. Kits may include chaotropic salts, polymers for matrix formation, and such containers as are required for gradient separation and isolation of fractions.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

EXPERIMENTAL

Materials and Methods

Preparation of dense chaotropic salt. RbTCA, CsTCA, BaTCA, RbSCN, CsSCN salts were dissolved in doubly deionized (MilliQ) water (dd $H_2O$). Solutions were titrated dropwise to pH 7.0 while the solution was purged by bubbling nitrogen gas ($N_2$). $N_2$ bubbling continued for at least 1 h after the pH stabilized. Norit activated carbon was added to the solution and the mixture allowed to sit overnight at room temperature. Activated carbon and other insoluble material was removed with a 0.22-μm filter and the solvent evaporated under vacuum. The resulting needle-like crystals were further dried over phosphorus pentoxide ($P_2O_5$) under vacuum until the mass of the solid became constant. The salt crystals were crushed to a fine powder using a mortar and pestle and stored over $P2O_5$ and under vacuum at room temperature. This powder is stable indefinitely at room temperature under these storage conditions.

Gradient preparation, DNA fractionation, and workup. Preparation of 5-molar salt solutions. Solid salt powder was weighed into a tube and dissolved in 30 mM Tris-Cl, 2.5 mM EDTA pH 8.0 (Buffer A) by vortexing. The refractive index of the buffered solution was adjusted to a value of 1.445 through addition of solid salt powder or dilution with Buffer A. In the case of RbTCA, according to Burke and Bauer (1), the target refractive index corresponds to a concentration of 5.063 M. The buffered salt solution was filtered using a 0.22-μm filter.

Genomic-DNA preparation. Fixed chromatinized DNA circles: Samples containing $10^5$ cells are fixed by adding formaldehyde drop-wise directly to the culture medium to a final concentration of 0.75% with gentle rotation at room temperature (RT) for 10 min to mix. Cells are pelleted by centrifugation (1,000×g) for 5 min and washed 3 times with cold phosphate-buffered saline, pH 7.4 (PBS). No sonication or fractionation is performed. Chromatin from any source, for example isolated nuclei, cells, soft or solid tissues, whole animals, fluids—urine, blood, plasma, saliva, semen, tears, menstrual blood etc. can be processed in this way. The method can be modified for size range and chromatin states of circular DNAs.

Naked DNA circles (including HMW circles >50 kbp): cells/tissues/any fluids/whole animals such as *C. elegans* worms can be used directly (incubated in salt solution) or in plugs consisting of hydrogel or pluronic matrices. DNA from any source, for example isolated nuclei, cells, soft or solid tissues, whole animals, fluids—urine, blood, plasma, saliva, semen, tears, cerebrospinal fluid, menstrual blood etc. can be processed in this way.

Naked DNA circles <50 kbp from cells/tissues/any fluids: Genomic DNA was prepared using DNeasy or MagAttract kits according to the manufacturer's protocols (Qiagen 69504 or 67563, respectively). Additional kits include but not limited to Zymo and Takara (D6060 and 740160.20). DNA from any source, for example isolated nuclei, cells, soft or solid tissues, whole animals, fluids—urine, blood, plasma, saliva, semen, tears, cerebrospinal fluid, menstrual blood etc. can be processed in this way.

Plasmid DNAs: DNA was prepared using Qiagen, Zymo, Takara/Clonetech, or Promega megaprep kits according to the manufacturer.

Ultracentrifugation and Fractionation: For micro-ultracentrifugation, gently mix the DNA sample (≥10 ng) with 220 µL of the buffered chaotropic salt solution (180/220 v/v=1.2 fold dilution). Similar dilution can be used for up to 2 mL final volume (based on the rotor chosen). For matrix-embedded samples, up to 113 mg of matrix may be used for 1 mL total volume. Additional matrix material can be used, provided larger final volume of the buffered salt solution is used, up to 2 mL. Add the plug slice directly to the salt solution and incubate at room temperature. Plugs that dissolve in the salt solution at room temperature release HMW DNA. The working solution is then transferred to the appropriate tube and placed in a fixed-angle rotor (including but not limited to: Beckman and Sorvall fixed-angle rotors, such as S120-VT) Ultracentrifugation in fixed angle rotors was carried out for 4-5 h at 80,000×g-200,000×g. Centrifuge tubes were carefully removed from the rotor using tweezers and transferred to a tube rack. For ultracentrifugation of a total volume of <1 mL, typically 5 unequal-volume fractions were withdrawn from each tube. All fractions were dispensed into sterile low-adhesion Eppendorf tubes. Fraction volumes should be adjusted based on the total volume of the gradient.

Sample Dialysis and Workup: Fractions were desalted using Pierce/ThermoFisher Slide-A-Lyzer disposable mini-dialysis chambers. Membranes in the chambers were rinsed with dd H$_2$O for 20 min to remove glycerol. The fractions were loaded into the prepared chambers, which were floated on ≈1.8 L of TE buffer in a 2-L beaker and dialyzed overnight at 4° C. with continuous stirring. Dialyzed fractions were transferred to low-adhesion Eppendorf tubes and the sample volume was reduced using a SuperVac 20 drying system.

Figure 2:
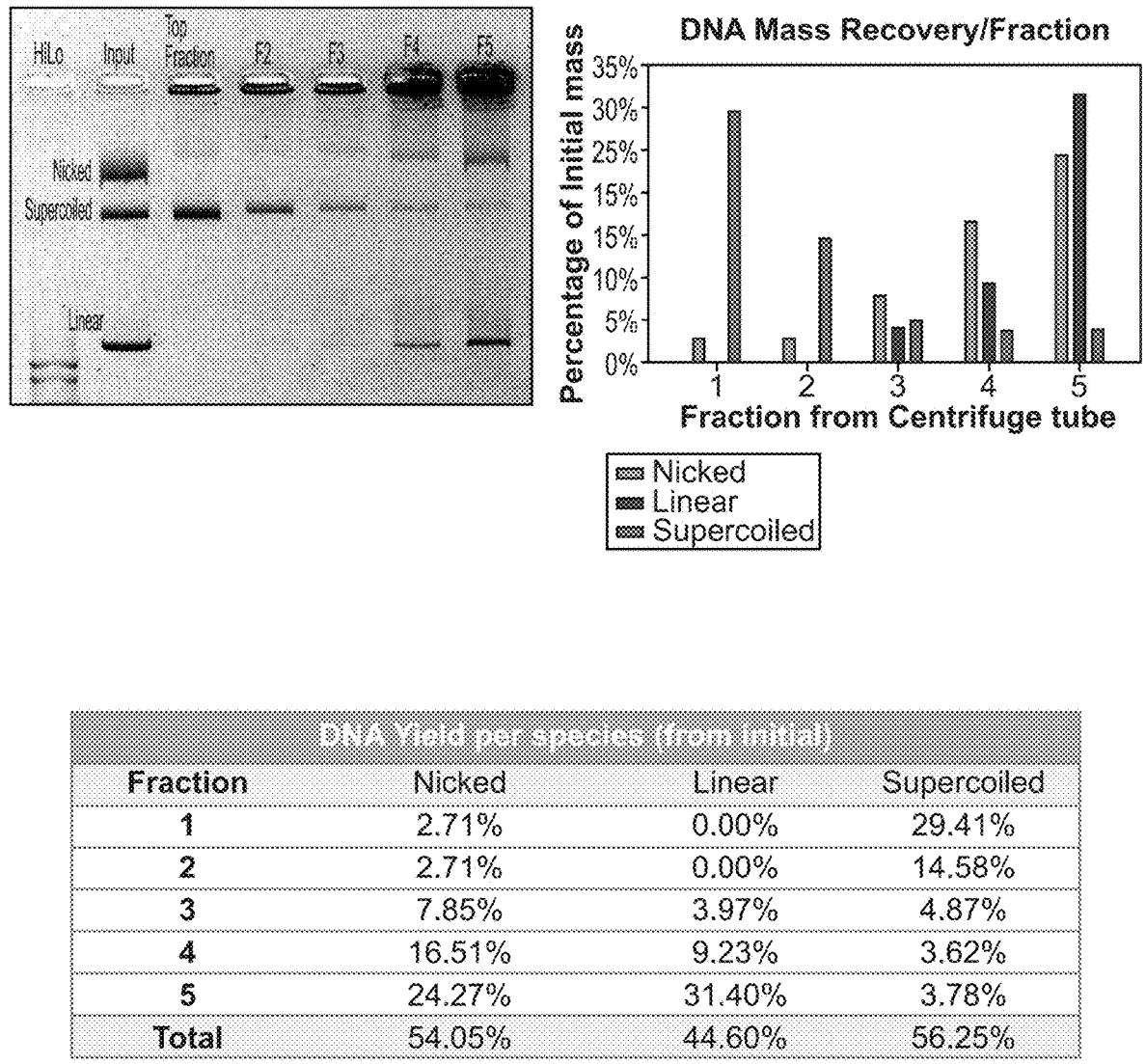
FIG. 2. Fractionation of different circular-DNA topological forms for a 13.0-kbp plasmid DNA according to the method described herein. Fractions of an equimolar mixture consisting of nicked (N), linear (L), and supercoiled (S) forms of a 13.0-kbp plasmid subjected to density-gradient centrifugation. The agarose gel shows the composition of fractions 1-5 (top to bottom of the gradient). The gel bands in the far-left lane are (top to bottom) N, S, L. The graph shows the relative abundance (mass fraction relative to DNA input of the given species) as a function of fraction number. Overall yield of each species is given in the bottom table FIG. 3. *C. elegans* eccDNA species (published protocol [Shoura et al. (2017) G3-Genes Genomes Genetics, October 5; 7(10):3295-3303] compared to the subject technology: We note that all fractions sequenced from the gradient map predominantly to the worm genome (>95% purity). Fractions 1 and 2 (red) are almost identical in coverage and correspond to known eccDNA regions (blue). Moreover, these fractions provide full coverage of the mtDNA (further confirming purification of circular DNAs). Additionally, we discover new regions of circular DNA not detected using previous methods.

Fraction analysis: Proof-of-principle experiments were carried out using an equimolar mixture of nicked, linear, and supercoiled forms of a 4.0-kbp control plasmid and were analyzed using agarose-gel electrophoresis combined with an in-house gel-quantitation plug-in program written for ImageJ {Ziraldo, 2019}. Fractionation efficiency and recovery of each form (supercoiled, nicked, and linear) were determined by the following methods. Fractionation efficiency was measured by the proportion of each species (supercoiled, nicked, or linear) in a particular gradient fraction from the ratio of integrated agarose-gel band intensity for a specific form relative to the total intensity for all three forms. Recovery of each species was found by comparing the total integrated intensity summed for all gradient fractions relative to that in the mixture of topological forms applied to the gradient, as shown in FIG. 1 and FIG. 2 respectively.

Circular DNA Purification and Sequencing: Ultracentrifugation and isolation of circular DNAs from *C. elegans*. The matrix-embedded lysate was dissolved in the gradient medium, the refractive index was adjusted to 1.445 as described above, and the mixture was transferred to a 220-µL tube. Ultracentrifugation and dialysis procedures were as described above and the supercoiled (covalently closed) or nicked circular DNA fraction was recovered from the gradient.

Figure 3:
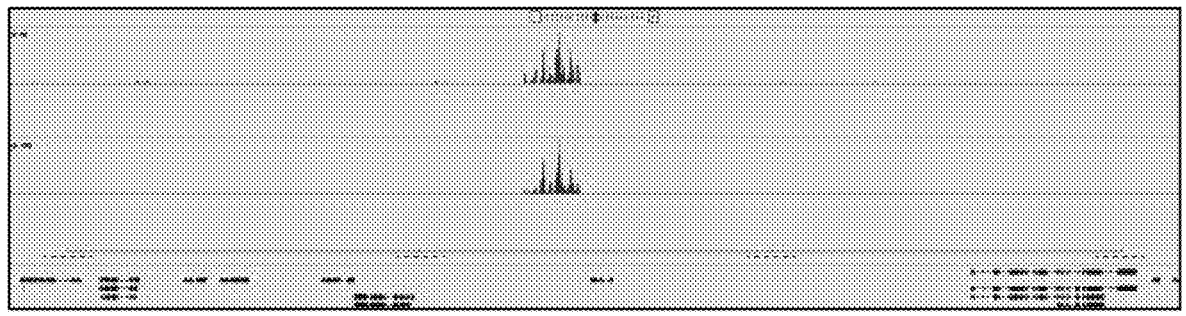
Figure 3:
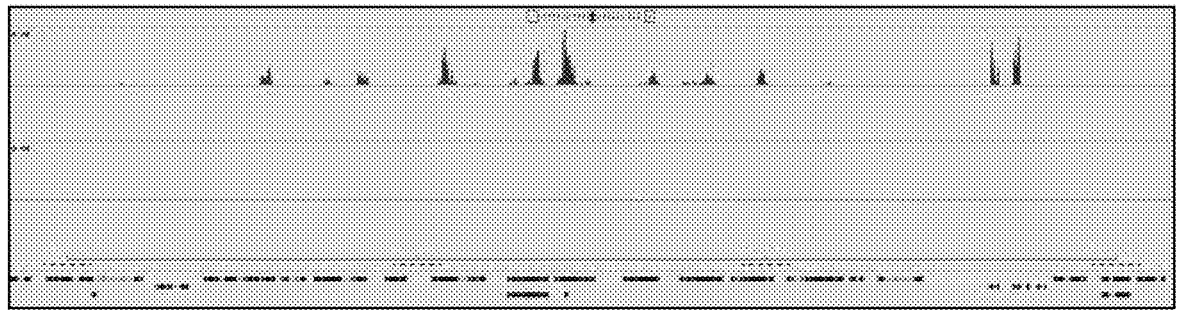

Sequencing Procedure and analysis. Libraries were prepared from the isolated fractions using Nextera Tn5 tagmentase (Illumina) as previously described by Shoura, et al. "Intricate and Cell Type-Specific Populations of Endogenous Circular DNA (eccDNA) in Caenorhabditis elegans and *Homo sapiens*." G3 (Bethesda). 2017; 7(10):3295-3303. Bioinformatic analyses to map circular species to a reference genome were also done as described by Shoura (2017). The results are shown in FIG. 3.

What is claimed is:

1. A method for topology-dependent, rapid DNA purification of circular DNA greater than 50 kbp in size; the method comprising:
    a) embedding cells in a polymer matrix;
    b) dissolving the polymer matrix in a chaotropic dense salt solution to lyse the cells in situ, thereby providing a DNA sample comprising circular DNA greater than 50 kbp in size in multiple topological states in the absence of intercalating dye and in the absence of protein-dependent digests;
    c) performing ultracentrifugation on the DNA sample in the chaotropic dense salt solution in the absence of intercalating dye;
    d) isolating fractions of DNA from a gradient of the DNA sample created by the ultracentrifugation;
    e) removing excess salt from the DNA fractions to generate a purified population of circular DNA greater than 50 kbp in size.

2. The method of claim 1, further comprising a step of characterization of the purified population of circular DNA using one or more of gel electrophoresis, capillary electrophoresis, single-molecule electrophoretic analysis, chromatography, high-resolution imaging, and NGS libraries/sequencing.

3. The method of claim 1, wherein the centrifugation is air-driven.

4. The method of claim 1, wherein the purified DNA population is fractionated into closed circular DNA, nicked circular DNA and linear DNA by the ultracentrifugation step.

5. The method of claim 1, wherein the DNA sample comprises less than 10 ng of DNA.

6. The method of claim 1, wherein the DNA sample comprises eukaryotic extra-chromosomal circular DNA (eccDNA), double-minute elements, or circular extrachromosomal DNA (ecDNA), microDNA, present as circular DNA greater than 50 kbp in size.

7. The method of claim 1, wherein the polymer matrix is selected from the group consisting of agarose, gelatin, polysaccharides, alginate; pluronic polymers or combinations thereof.

8. The method of claim 1 where the DNA topology and size is maintained following step (a).

9. The method of claim 1, wherein step (b) is performed at room temperature.

10. The method of claim 1 where the DNA sample is nuclear DNA or circulating DNA.

11. The method of claim 1 where the DNA sample consists of cells, hard tissues, soft tissues, whole organisms, or a bodily fluid.

12. The method of claim 1 wherein the DNA sample comprises fixed chromatin.

13. The method of claim 12, wherein the purified population of circular DNA following step (e) maintains structure of the chromatin.

14. The method of claim 13, where chromatin marks and modification on purified circular DNAs are maintained and analyzed post purification.

15. The method of claim 12, wherein the chromatin is immunoprecipitated or affinity-isolated and selected for marks and modification pre- or post-circular DNA purification.

16. The method of claim 1, wherein the DNA sample comprises methylated DNA, histone modifications, methylation and modification patterns that are preserved during purification; and are assayed post or prior to processing.

17. The method of claim 1, wherein the DNA sample is spiked with circular DNA standards of known size, topology, sequence, and copy number.

18. The method of claim 1, wherein the chaotropic dense salt solution is Rb trichloroacetic acid (TCA), CsTCA, BaTCA, Rb thiocynanate (SCN), or CsSCN salt or a combination thereof.

19. The method of claim 1, wherein the DNA sample is isolated from an individual with cancer.

20. The method of claim 1, wherein the DNA sample comprises supercoiled DNA.

21. The method of claim 1, wherein steps (a) to (e) are performed at a pH of 6-12.

* * * * *